United States Patent [19]

Kalk et al.

[11] 4,102,924
[45] Jul. 25, 1978

[54] PROCESS FOR THE PREPARATION OF DIARYL COMPOUNDS

[75] Inventors: Walter Kalk, Opladen; Hans Samuel Bien, Burscheid; Karl Heinz Schundehutte, Opladen, all of Germany

[73] Assignee: Bayer Aktiengesellschaft, Leverkusen, Germany

[21] Appl. No.: 620,314

[22] Filed: Oct. 7, 1975

Related U.S. Application Data

[62] Division of Ser. No. 515,222, Oct. 16, 1974, abandoned.

[30] Foreign Application Priority Data

Oct. 25, 1973 [DE] Fed. Rep. of Germany ....... 2353580

[51] Int. Cl.² .......................................... C07C 103/34
[52] U.S. Cl. ............................ 260/562 P; 260/558 P;
260/562 A; 260/562 R
[58] Field of Search ........... 260/562 P, 562 A, 562 R,
260/558 P

[56] References Cited
FOREIGN PATENT DOCUMENTS 2,250,106  4/1973  Fed. Rep. of Germany.

OTHER PUBLICATIONS

Bell, J. Chem. Soc., 1934, pp. 835–838.
Mascarelli et al., Chem. Abstract, 1938, col. 4565–4566.
Migrdichian, Organic Synthesis, vol. 2, Reinhold Publishing Corp., N.Y., N.Y., pp. 1225–1226, (1957).
Krauch et al., Organic Name Reactions, John Wiley & Sons, N.Y., 1965, pp. 463–464.
Fanta, Chem. Rev., 38 (1946), pp. 140–149, 188, 189.

*Primary Examiner*—Arthur P. Demers
*Attorney, Agent, or Firm*—Plumley and Tyner

[57] ABSTRACT

Process for the preparation of diaryl compounds of the formula

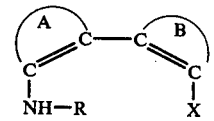

by reacting of acylamino-aryl-compounds of the formula

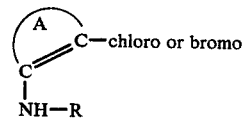

with aryl compounds of the formula

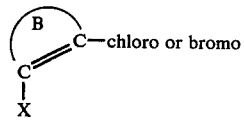

in the presence of metallic copper or its mixture with copper salts, optionally in the presence of catalysts, in a solvent which is inert under the reaction conditions, at temperatures of 20° to 200° C. In the formulae A and B represent an aromatic ring system, R represents acyl and X represents a nitro, nitrile, carboxylic ester, acyl or —NH—R group.

8 Claims, No Drawings

PROCESS FOR THE PREPARATION OF DIARYL COMPOUNDS

This is a division of application, Ser. No. 515,222 filed Oct. 16, 1974 now abandoned.

The invention relates to a new process for the preparation of diaryl compounds of the formula

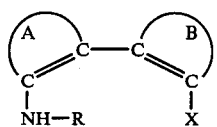
(I)

in which
A represents a monocyclic or bicyclic aromatic carbocyclic ring system, preferably a benzene or naphthalene ring, or a monocyclic or polycyclic aromatic heterocyclic ring system, preferably a 5-membered or 6-membered hetaryl ring which optionally possesses a fused benzene ring.
B represents a monocyclic or polycyclic aromatic carbocyclic or heterocyclic ring system, preferably a benzene or naphthalene ring, or a 5-membered or 6-membered hetaryl ring which optionally possesses a fused benzene ring, the ring systems A and B can possess non-ionic and/or ionic substituents,
R represents an acyl radical, preferably the radical of an aliphatic monocarboxylic acid and
X represents the nitro or nitrile group, a carboxylic acid ester group, an acyl group or the —NH—R group. In the process, acylamino-aryl compounds of the formula

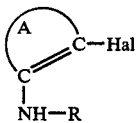
(II)

in which
A and R have the meaning indicated under the formula I Le A 15 284 and
Hal represents a chlorine or bromine atom are reacted with aryl compounds of the formula

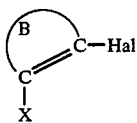
(III)

in which
B and X have the meaning indicated under the formula I and
Hal represents a chlorine or bromine atom in the presence of metallic copper, in a solvent which is inert under the reaction conditions, at temperatures of 20° to 200° C, preferably 50° to 150° C.

Possible ring systems A and B are, above all: as monocyclic aromatic carbocyclic ring systems, the benzene ring; as bicyclic aromatic carbocyclic ring systems, the naphthalene ring; as polycyclic aromatic carbocyclic ring systems, the anthracene, anthraquinone or phenanthrene ring, but especially the naphthalene ring; as monocyclic aromatic heterocyclic ring systems, 5- and 6-membered heteryl rings, such as the thiophene, thiazole, pyrazole, pyridine, pyrazine, pyridazine or pyrimidine ring; as polycyclic aromatic heterocyclic ring systems, 5-membered and 6-membered heteryl rings with fused benzene rings, for example the quinoline, isoquinoline, indazole and thionaphthene ring.

The abovementioned ring systems can possess non-ionic and/or ionic substituents. As non-ionic substituents there should above all be mentioned: alkyl groups, such as the methyl, ethyl, n- and i-propyl and n-, i-, sec.- or tert- butyl group; alkoxy groups, such as the methoxy, ethoxy, propoxy or butoxy group; the nitro, hydroxyl and nitrile group; carboxylic acid ester groups, such as the methoxycarbonyl, ethoxycarbonyl, benzyloxycarbonyl or phenoxycarbonyl group; the amino group; monoalkylamino and dialkylamino groups, such as the monomethylamino, diethylamino and monobutylamino group; acylamino groups, such as the formyl-, acetyl-, propionyl-, butyryl-, benzoyl-,methanesulphonyl and benzenesulphonyl-amino group; alkanesulphonyl groups, such as the methanesulphonyl and ethanesulphonyl group; the trifluoromethyl group; or halogen atoms, such as fluorine, chlorine or bromine atoms.

The carboxyl and the sulphonic acid groups may be mentioned as ionic substituents.

Acyl radicals R which may be mentioned are: radicals of optionally substituted aliphatic carboxylic acids, above all of lower aliphatic monocarboxylic acids, such as the formyl, acetyl, acetoacetyl, propionyl, butyryl, pentanecarbonyl and hexanecarbonyl radical; the CO—COOH radical; radicals of cycloaliphatic carboxylic acids, such as the cyclohexanecarbonyl radical; radicals of araliphatic carboxylic acids, such as the phenylacetyl and β-phenylpropionyl radical; radicals of aromatic carboxylic acids, for example the benzoyl radical substituted by $C_1$-$C_4$-alkyl, $C_1$-$C_4$-alkoxy, nitro and/or halogen, such as the benzoyl, toluyl, 4-chlorobenzoyl, 3-bromo-benzoyl, 4-methoxy-benzoyl and 4-nitrobenzoyl radical; the radical of sulphuric acid, —$SO_3H$; radicals of aliphatic, araliphatic and aromatic sulphonic acids, such as the methanesulphonyl, ethanesulphonyl, hexanesulphonyl, phenylmethanesulphonyl, benzenesulphonyl and toluenesulphonyl radical; of N,N-dialkyl-sulphamic acid, such as the dimethylaminosulphonyl, diethylaminosulphonyl and di-n-butylaminosulphonyl radical; aminocarbonyl, N-alkylaminocarbonyl and N,N-dialkylaminocarbonyl radicals, such as the carbamoyl, N-methylamino-carbonyl, N,N-diethylamino-carbonyl, N-butylamino-carbonyl and N,N-dibutylamino-carbonyl radical; alkoxycarbonyl radicals, such as the methoxycarbonyl, ethoxycarbonyl, propoxycarbonyl and butoxycarbonyl radical; aralkoxycarbonyl radicals, such as the benzyloxycarbonyl radical and the derivatives substituted in the phenyl ring by $C_1$-$C_4$-alkyl groups and/or halogen atoms; and aroxycarbonyl radicals, such as the phenoxycarbonyl radical and its derivatives substituted in the phenyl ring by $C_1$-$C_4$-alkyl groups and/or halogen atoms.

For X there may be mentioned: as carboxylic acid ester groups, above all $C_1$-$C_4$-alkoxycarbonyl groups, such as the methoxycarbonyl and ethoxycarbonyl group and aralkoxy groups, such as the benzyloxycarbonyl group and its derivatives substituted in the phenyl ring by $C_1$-$C_4$-alkyl groups and/or halogen atoms; as acyl groups, above all the radicals of aliphatic, cycloaliphatic, araliphatic and aromatic carboxylic acids, such as the acetyl, propionyl, cyclohexanecarbonyl, phenylacetyl and benzoyl radical and its derivatives substituted in the phenyl ring by non-ionic substituents.

The process according to the invention is usually carried out by dissolving the starting compounds of the formula II and III in the organic solvents which are optionally diluted with water, warming the solutions to the reaction temperature, then adding the copper powder and completing the reaction by stirring for several hours at elevated temperatures. The reaction solution is then decoppered in the manner customary for Ullmann reactions by addition of, for example, hydrochloric acid, aqueous ammonia or sodium thiosulphate. Hereupon, the diaryl compounds of the formula I separate out quantitatively as solids and are separated off by filtration.

The process according to the invention can also be carried out by first taking the copper powder as a suspension in the solvent, heating the suspension to the desired reaction temperature and then introducing the starting compounds of the formula II and III. Using either one or the other procedure, the starting compounds II and III are employed in the molar ratio of about 1:1.

In many cases it has proved advantageous to carry out the reaction in the presence of a catalyst, for example catalytic amounts of halogen, preferably iodine.

The metallic copper is usually employed in the form of copper powder; however, in some cases the use of mixtures of copper powder and copper salts, for example copper-I salts and copper-I oxide, has proved of value.

The copper is usually employed in an amount equivalent to the halogen to be split off; the use of an excess of copper, of about 10 to 20%, can, however, be advantageous in many cases since the yield can be increased thereby.

Polar organic solvents have proved particularly successful as solvents in the process according to the invention; examples are dimethylformamide, dimethylacetamide, N-methylpyrrolidone, dimethylsulphonic, sulpholane, phosphoric acid tris-dimethylamide or nitrobenzene. The watermiscible solvents can also be used as a mixture with water.

Using the process according to the invention, symmetrical and asymmetrical diaryl compounds of the formula I are obtained in a simple manner, under gentle conditions, in high purity and good yields. The symmetrical compounds are produced by reaction of compound II and III, if in III B = A and X = NHR. The diaryl compounds of the formula I are important intermediate products, for example for the preparation of dyestuffs.

The following may be mentioned as examples of starting materials of the formula II: 2-chloro-acetanilide, 2-chloroformylanilide, 2-bromo-propionylanilide, 1-bromo-2-methoxycarbonylamino-benzene, 1-bromo-2-methanesulphonylamino-benzene, 2-chlorobutyrylanilide, 1-bromo-2-ethoxycarbonylamino-5-methyl-benzene, 2,4-dichloro-acetanilide, 2-bromo-4-chloropropionylanilide, 2-chloro-4-nitro-acetanilide, 2-bromoformylanilide, 2-bromo-acetanilide, 2-bromo-3-chloro-propionylanilide, 2-bromo-5-chloro-butyrylanilide, 2-bromo-6-chloroacetanilide, acetoacetic acid 2-bromo-5-chloro-anilide, 2-bromo-benzoylanilide, 2-bromo-5-chloro-benzoyl-anilide, 4-chloro-6-bromo-2-nitro-acetanilide, 2-bromo-6-methyl-acetanilide, 2-bromo-6-methoxy-acetanilide, 2-bromo-5-methyl-propionylanilide, 2-bromo-5-ethoxy-acetanilide, 2-bromo-5-trifluoromethyl-acetanilide, 2-bromo-5-methoxycarbonyl-acetanilide, 2-bromo-4-chloro-5-methyl-acetanilide, 2-bromo-4-chloro-5-methoxypropionylanilide, 2-bromo-4-nitro-5-methyl-acetanilide, 2-bromo-4-amino-5-chloro-acetanilide, 2-bromo-4-acetylamino-6-chloro-acetanilide, 2-bromo-4-dimethylamino-5-chlorobutyrylanilide, 2-bromo-4-acetylamino-6-chloro-acetanilide, 2-bromo-4-hydroxy-acetanilide, 2-bromo-4-methoxy-acetanilide, 2-bromo-4-methanesulphonyl-benzoylanilide, 2-bromo-5-methoxyacetanilide, 2-bromo-4-methoxy-5-acetylamino-acetanilide, 2-bromo-4-chloro-5-acetylamino-acetanilide, 2-bromo-5-diethylamino-acetanilide, 2-bromo-4-diethylamino-methansulphonylanilide, 2,4-dibromoacetanilide, 2-bromo-4-nitro-acetanilide, 2-bromo-4-carboxyl-acetanilide, 3-bromo-4-acetylaminobenzoic acid, 3-bromo-4-acetylamino-benzenesulphonic acid, 2-bromo-5-acetylamino, 2-bromo-4-acetylaminoacetanilide, 2-bromo-4-methanesulphonylamino-acetanilide, 1,6-dibromo-2-acetylamino-naphthalene, 2,4-dibromo-1-acetylaminonaphthalene, 1-bromo-2-acetylamino-6-nitronaphthalene, 2-bromo-4-nitro-formylaniline, 3,5-dibromo-2-acetylaminopyridine, 2-acetylamino-3-bromo-pyridine, 2-formylamino-3-bromo-pyridine 4-benzoylamino-3-bromo-pyridine, 2-bromo-3-acetylamino-quinoline, 3-bromo-4-acetylamino-quinoline, 3-bromo-4-butyrylamino-quinoline, 6,8-dibromo-5-acetylaminoquinoline, 5-bromo-6-propionylamino-quinoline, 5,8-dibromo-6-acetylamino-quinoline, 7-bromo-8-acetylamino-quinoline, 7-bromo-8-dimethylaminocarbonylamino-quinoline, 5,7-dibromo-8-acetylamino-quinoline, 4-bromo-5-acetylamino-isoquinoline, 3-formylamino-4-bromo-isoquinoline, 4-acetylamino-5-bromopyrimidine, 2-acetylamino-3-bromo-pyrazine, 1-phenyl-3-methyl4-bromo-5-acetylamino-pyrazole, 4-bromo-5-acetylamino-benzo[b]thiophene, 2,5-dichloroacetanilide; 2,4,5-trichloroacetanilide; 2-chloro-4-nitro-formanilide; 4,6-dichloro-2-nitro-acetanilide; 3-chloro-2-acetamino-toluene, 4-chloro-3-acetamino-toluene; 4,6-dichloro-3-acetamino-toluene; 4-chloro-6-nitro-3-acetaminotoluene; 2.5-dichloro-4-amino-acetanilide; 2-chloro-4-methoxyacetanilide.

As starting compounds of the formula III it is possible to use the compounds mentioned above for formula II, and additionally also o-nitro-chlorobenzene, 2-nitro-bromobenzene, 2,3-dichloro-1-nitro-benzene, 2,4-dichloro-1-nitro-benzene, 2,5-dichloro-1-nitro-benzene, 2,4,5-trichloro-1-nitro-benzene, 3,5-dichloro-1,2-dinitro-benzene, 2-chloro-1,3-dinitrobenzene, 2,4,5-trichloro-1,3-dinitro-benzene, 4-chloro-3-nitro-toluene, 4-chloro-3-nitro-benzotrifluoride, 4,6-dichloro-3-nitrotoluene, 4-chloro-3-nitro-phenol, 3-chloro-4-nitrophenol, 2,5-dibromo-1-nitro-benzene, 2,4,6-trinitrochlorobenzene, 2-bromo-4,5-dimethoxy-1-nitrobenzene, 2-bromo-5-nitro-benzoic acid methyl ester, 2-chloro-3-nitrobenzoic acid ethyl ester, 1-bromo-2-naphthoic acid methyl ester, 2-bromo-3-naphthoic acid methyl ester, 2-bromo-benzoic acid methyl ester, 2-chloro-benzoic acid methyl ester, 2-bromo-5-methoxy-6-methylbenzoic acid methyl ester, 2,4-dichloro-benzoic acid methyl ester, 2,5-dichlorobenzoic acid methyl ester, 2-chloro-5-nitro-benzoic acid methyl ester, 2-chloro-benzonitrile, 2-chloro-5-nitro-benzonitrile, 2-chloro-4-nitro-benzonitrile, 2-bromo-4-fluoro-benzophenone, 2-bromo-3'- methyl-benzophenone, 2-bromo-4'-methyl-benzophenone, 2-bromo-4'-methoxy-benzophenone, 2-bromo-4'-methyl-benzophenone, 2-bromo-4'-methoxy-benzophenone, 1,2-dibromo-anthraquinone, 1,3-dibromo-anthraquinone, 1-bromo-3-methyl-anthraquinone, 1-chloro-4-methyl-anthraquinone, 1-chloro-anthraquinone, 1-bromo-anthraquinone and 1-bromo-2-acetylamino-anthraquinone.

It is known from the literature to prepare diaryl compounds by Ullmann reaction, that is to say by reaction of aromatic halogen compounds in the presence of metallic copper, at elevated temperature. The reactive iodine compounds are particularly suitable for the reaction, whilst bromobenzenes and chlorobenzenes only react of activating substituents are present in the o-position relative to the halogen atom. Electron-attracting substituents, such as the nitro, nitrile and carbonyl group, are known as such activating substituents. Deactivating substituents, such as the acylamino group, inhibit the Ullmann reaction (see P.E. Fanta, Chem. Reviews. 38 (1946), page 140).

The processes described in DT-OS (German Published Specification) Nos. 1,944,276, 1,955,157, 1,956,236, 2,250,106 and 2,250,107 for the preparation of 2,2'-diacylamino-1,1'-dianthraquinonyls are examples of the known Ullmann reaction. Here, the halogen atom present in the 1-position is activated by the carbonyl group in the ortho-position.

In contrast, in the process according to the invention, a halogen compound of which the halogen atom is not activated by the known electron-attracting substituents, is used in the starting compounds II. The course of the process according to the invention is therefore surprising. It was to be expected that the acylamino group in the ortho-position to the carbon atom carrying the halogen inhibit the course of the Ullmann reaction. Instead of this it was found that it activates the halogen atom comparably to the known electronattracting substituents, so that the reaction takes place smoothly and under mild conditions.

Furthermore, it is known from the literature that o-acylaminohalogenobenzenes, on heating in organic solvents in the presence of copper salts, form benzoxazoles (see, for example, U.S. Pat. No. 3,147,253, and Dt-PS (German Published Specification Nos.) 1,445,916 and 1,795,654). Hence, it was surprising that the process according to the invention produces bis-aryl compounds whilst the intramolecular cyclisation to the oxazole, which was to be expected, virtually does not occur.

EXAMPLE 1

102 g of 2,4-dichloroacetanilide, prepared by acetylation of 2,4-dichloroanidinne, are heated in 100 ml of dimethylformamide, to 150° C. At this temperature, 38 g of copper powder are added and the mixture is stirred for 4 hours at 150° C. After cooling to room temperature, the reaction mixture is freed from copper by stirring with hydrochloric acid.

46 g (55% of theory) of 2,2'-bis-(acetylamino)-5,5'-dichloro-biphenyl of the formula

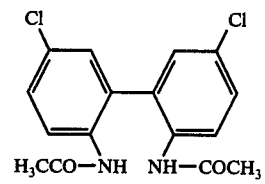

are obtained.

If instead of 2,4-dichloroacetanilide the equivalent amount of a ) 2-chloro-acetanilide or b) 2-chloro-4-nitroacetanilide was used, the following diphenyl derivatives were obtained: a) 2,2'-bis-(acetylamino)-diphenyl, and b) 2,2'-bis-(acetylamino)-5,5'-di-nitro-diphenyl.

If instead of the N-acetanilides used, the corresponding N-formylanilides, N-benzoylanilides or N-ethoxycarbonyl-anilides were employed, the corresponding formylamino-, benzoylamino- or ethoxycarbonylamino-diphenyl derivatives were obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 2

124 g of 2-bromo-4-chloro-acetanilide, obtained by bromination of 4-chloro-acetanilide, in 125 ml of dimethylformamide are heated to 100° C. At this temperature, 38 g of copper powder are added and the mixture is stirred for 3 hours at 100° C. After cooling to room temperature, the reaction mixture is freed from copper by stirring with an aqueous solution of sodium thiosulphate.

71 g (85% of theory) of 2,2'-bis-(acetylamino)-5,5'-dichlorobiphenyl of the formula

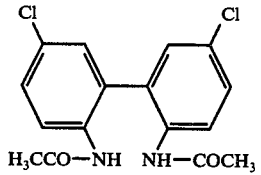

are obtained.

If 0.1 g of iodine were added as a catalyst to the reaction mixture, it was possible to carry out the reaction even at 80° C.

If instead of 2-bromo-4-chloro-acetanilide the equivalent amount of one of the acetanilides listed in column A of the table which follows was employed, the biphenyl derivatives described in column B were obtained.

| Table accompanying Example 2: | |
|---|---|
| A | B |
| 2-Bromo-acetanilide | ![biphenyl with H3CCO—NH NH—COCH3] |

-continued

Table accompanying Example 2:

| A | B |
|---|---|
| 2-Bromo-3-chloro-acetanilide | 2,2'-bis(chloro) biphenyl with H₃CCO—NH and NH—COCH₃ at 6,6' positions (Cl at 2,2') |
| 2-Bromo-5-chloro-acetanilide | Biphenyl with Cl at 4,4' and H₃CCO—NH, NH—COCH₃ at 2,2' |
| Acetoacetic acid 2-bromo-5-chloro-anilide | Biphenyl with Cl at 4,4' and H₃CCOCH₂CO—NH, NH—COCH₂COCH₃ at 2,2' |
| 2-Bromo-6-chloro-acetanilide | Biphenyl with Cl at 3,3' and H₃CCO—NH, NH—COCH₃ at 2,2' |
| 2-Bromo-4,5-dichloro-acetanilide | Biphenyl with Cl at 4,5 and 4',5' and H₃CCO—NH, NH—COCH₃ at 2,2' |
| 4-Chloro-6-bromo-2-nitro-acetanilide | Biphenyl with Cl at 5,5', O₂N at 3,3', and H₃CCO—NH, NH—COCH₃ at 2,2' |
| 3-Bromo-2-acetamino-toluene | Biphenyl with H₃C at 3,3' and H₃CCO—NH, NH—COCH₃ at 2,2' |
| 4-Bromo-3-acetamino-toluene | Biphenyl with H₃C at 4,4' and H₃CCO—NH, NH—COCH₃ at 2,2' |
| 4-Bromo-3-acetamino-benzotrifluoride | Biphenyl with F₃C at 4,4' and H₃CCO—NH, NH—COCH₃ at 2,2' |

-continued

Table accompanying Example 2:

| A | B |
|---|---|
| 4-Bromo-6-chloro-3-acetamino-toluene | 5,5'-dichloro-4,4'-dimethyl-2,2'-bis(acetylamino)biphenyl (Cl, H₃C, H₃CCO—NH on each ring) |
| 4-Bromo-6-nitro-3-acetamino-toluene | 5,5'-dinitro-4,4'-dimethyl-2,2'-bis(acetylamino)biphenyl (NO₂, H₃C, H₃CCO—NH on each ring) |
| 2-Bromo-5-chloro-4-amino-acetanilide | 5,5'-diamino-4,4'-dichloro-2,2'-bis(acetylamino)biphenyl (H₂N, Cl, H₃CCO—NH on each ring) |
| 2-Bromo-6-chloro-1,4-bis-(acetylamino)-benzene | biphenyl with H₃CCO—NH at 4,4'; Cl at 3,3'; H₃CCO—NH at 2,2' |
| 3-Bromo-4-acetamino-phenol | 5,5'-dihydroxy-2,2'-bis(acetylamino)biphenyl (OH, H₃CCO—NH on each ring) |
| 2-Bromo-4-methoxy-acetanilide | 5,5'-dimethoxy-2,2'-bis(acetylamino)biphenyl (H₃CO, H₃CCO—NH on each ring) |
| 2-Bromo-5-methoxy-acetanilide | 4,4'-dimethoxy-2,2'-bis(acetylamino)biphenyl (H₃CO, H₃CCO—NH on each ring) |
| 2-Bromo-4-methoxy-5-acetylamino-acetanilide | biphenyl with OCH₃ at 5,5'; H₃CCOHN at 4,4'; H₃CCO—NH at 2,2'; NHCOCH₃ at 4,4' |
| 2-Bromo-4-chloro-5-acetylamino-acetanilide | biphenyl with Cl at 5,5'; H₃CCOHN at 4,4'; H₃CCO—NH at 2,2'; NHCOCH₃ at 4,4' |

-continued

Table accompanying Example 2:

| A | B |
|---|---|
| 2-Bromo-5-diethylamino-acetanilide | (see structure) |
| 2-Bromo-4-diethylamino-acetanilide | (see structure) |

Instead of the N-acetyl starting compounds, the corresponding N-formyl, N-propionyl, N-butyryl, N-benzoyl, N-alkoxycarbonyl, dimethylaminocarbonylamino and methanesulphonylamino compounds were employed with equal success.

Instead of dimethylformamide, the solvents mentioned in Example 1 were employed as solvents with equal success.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 3

146 g of 2,4-dibromo-acetanilide, prepared by bromination of acetanilide, are heated, in 200 ml of dimethylformamide, to 100° C. 38 g of copper powder are added at this temperature. The mixture is then stirred for a further 3 hours at 100° C. Thereafter the reaction mixture is cooled to room temperature and is then freed from copper by addition of concentrated ammonia. 85 g (80% of theory) of 2,2'-bis-(acetylamino)-5,5'-dibromo-diphenyl of the formula

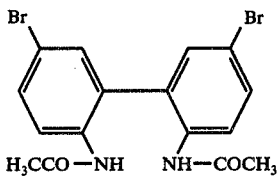

are obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 4

130 g of 2-bromo-nitro-acetanilide, obtained by acetylation of 2-bromo-aniline, are heated, in 200 ml of dimethylformamide, to 100° C. At this temperature, 38 g of copper powder are added and the reaction mixture is then stirred for 3 hours at 100° C. After cooling to room temperature, copper is removed in accordance with the process indicated in Example 2. 81.5 g (91% of theory) of 2,2'-bis-(acetylamino)-5,5'-dinitro-biphenyl of the formula

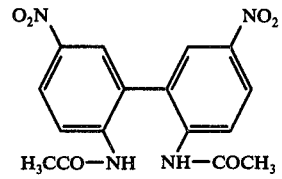

are obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 5

136 g of 4-bromo-N,N'-bisacetyl-1,3-phenylenediamine, prepared by bromination of N,N'-bisacetyl-1,3-phenylenediamine, are heated, in 300 ml of dimethylformamide, to 100° C. After adding 38 g of copper powder, the reaction mixture is stirred for 4 hours at 100° C. After cooling to room temperature, the mixture is freed from copper as indicated in Example 2. 72 g (75% of theory) of 2,2',4,4'-tetrakis-(acetylamino)-biphenyl of the formula

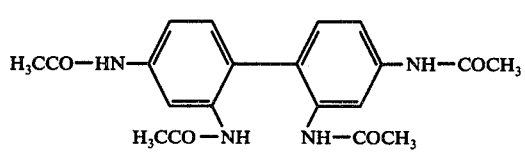

are obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 6

136 g of N,N'-diacetyl-2-bromo-1,4-phenylenediamine, prepared by bromination of N,N'-diacetyl-1,4-phenylenediamine, are heated, in 250 ml of dimethylformamide, to 100° C, and 38 g of copper powder are then added. The mixture is stirred for 3 hours at 100° C. After cooling to room temperature, the reaction mixture is freed from copper as described in Example 2. 2,2,',5,5'-Tetrakis-(acetylamino)-biphenyl of the formula

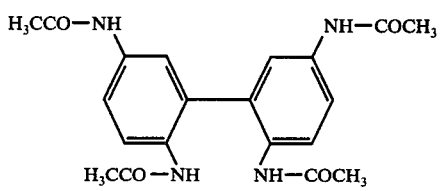

is obtained

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 7

172 g of 1,6-dibromo-2-acetylamino-naphthalene, obtained by bromination of 2-acetylamino-naphthalene, are warmed, in 250 ml of dimethylformamide, to 100° C. After addition of 38 g of copper powder, the reaction mixture is stirred for 3 hours at 100° C. After cooling to room temperature, copper is removed as described in Example 2. 2,2'-Bis-(acetylamino)-6,6'-dibromo-dinaphthyl-(1,1') of the formula

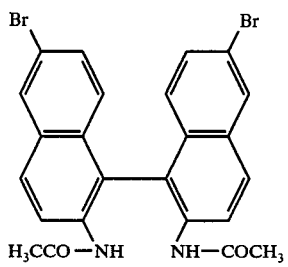

is obtained.

Instead of dimethylformamide, dimethylsulphoxide, dimethylacetamide, N-methylpyrrolidine, phosphoric acid trisdimethylamide or sulpholane were also used, with equal success, as the solvent.

EXAMPLE 8

172 g of 2,4-dibromo-1-acetylamino-naphthalene, prepared by bromination of 1-acetylamino-naphthalene, are warmed, in 300 ml of dimethylformamide, to 100° C. 38 g of copper powder are then added and thereafter the mixture is stirred for 3 hours at 100° C. After cooling to room temperature, the reaction mixture is freed from copper as described in Example 2. 1,1'-Bis-(acetylamino)-4,4'-dibromo-dinaphthyl(2,2') of the formula

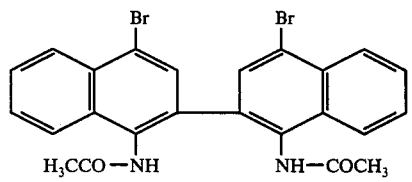

is obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 9

155 g of 1-bromo-2-acetylamino-6-nitro-naphthalene, prepared by nitration of 1-bromo-2-acetylamino-naphthalene, are heated, in 300 ml of dimethylformamide, to 100° C, and 38 g of copper powder are then added. After stirring for 3 hours at this temperature, the reaction mixture is allowed to cool to room temperature and is freed from copper as described in Example 2. 2,2'-Bis-(acetylamino)-6,6'-dinitro-dinaphthyl-(1,1') of the formula

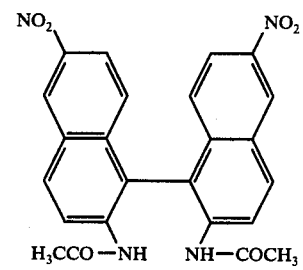

is obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 10

15.7 g of o-nitro-chlorobenzene and 24.8 g of 2-bromo-4-chloroacetanilide are heated, in 40 ml of dimethylformamide, to 150° C. 15.2 g of copper powder are added and the mixture is stirred for 2 hours at 150° C. After cooling to room temperature, copper is removed as described in Example 2. 2-Acetylamino-2'-nitro-5-chloro-biphenyl of the formula

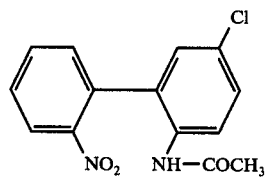

is obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 11

24.8 g of 2-bromo-4-chloro-acetanilide and 17.0 g of 2-chloro-acetanilide are heated, in 40 ml of dimethylformamide, to 150° C. 15.2 g of copper powder are then added and the mixture is stirred for 2 hours at 150° C. After cooling to room temperature, copper is removed as described in Example 2. 2,2'-Bis-(acetylamino)-5-chloro-biphenyl of the formula

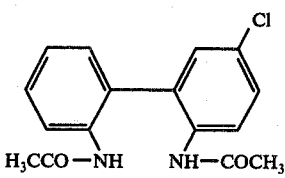

is obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 12

61 g of 2-bromo-4-nitro-formanilide and 158 g of o-nitrochlorobenzene are heated to 150° C. After adding 19 g of copper powder and 1.9 g of CuCl, the mixture is stirred at 150° C for 6 hours. It is allowed to cool and the excess o-nitrochlorobenzene is removed by steam distillation. The crude product is freed from copper in accordance with the process described in Example 2. 2-Formamino-5-nitro-2'-nitro-biphenyl of the formula

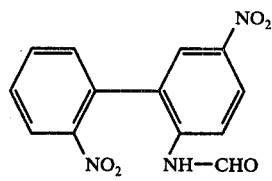

is obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 13

88 g of 1-phenyl-3-methyl-4-bromo-5-acetylaminopyrazole are heated, in 130 ml of dimethylformamide, to 90° C. After addition of 23 g of copper powder and 2 g of CuCl, the mixture is stirred for 6 hours at 90° C. It is then allowed to cool to room temperature and freed from copper by means of aqueous hydrochloric acid. A bis-pyrazolyl derivative of the formula

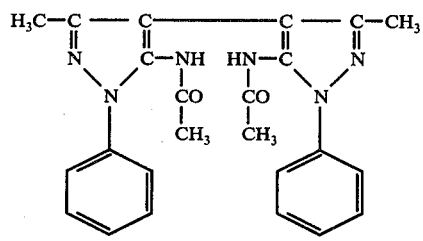

is obtained.

Instead of dimethylformamide, dimethylsulphoxide, dimethylacetamide, N-methylpyrrolidone, phosphoric acid trisdimethylamide or sulpholane were also used, with equal success, as the solvent.

EXAMPLE 14

21.8 g of 2,4-dichloro-5-methyl-acetanilide are heated, in 50 ml of dimethylformamide, to 150° C. After adding 7.6 g of copper powder, the mixture is stirred for 6 hours at 150° C. After cooling to room temperature, copper is removed in accordance with the process indicated in Example 2. 2,2'-Bis-(acetylamino)-4,4'-dimethyl-5,5'-dichlorobiphenyl of the formula

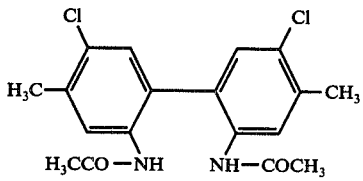

is obtained.

Instead of dimethylformamide, dimethylsulphonide, dimethylacetamide, N-methylpyrrolidone, phosphoric acid trisdimethylamide or sulpholane were also used, with equal success, as the solvent.

EXAMPLE 15

62 g of 2-bromo-4-chloro-acetanilide are dissolved in 65 ml of dimethylsulfoxide at 50° C. At this temperature 15.9 g of copper powder are added and the mixture is stirred at 4 hours at 50° C. The solvent is destillated in a vacuo. The remaining mixture is freed from copper by stirring with hydrochloric acid.

37 g (88% of theory) of the compound of example 1 are obtained.

We claim:

1. Process for preparing diaryl compounds of the formula

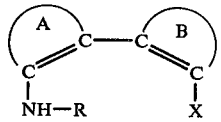

by reacting acylamino-aryl compound of the formula

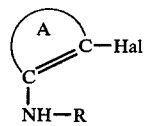

with an aryl compound of the formula

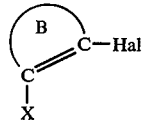

wherein
X is —NHR;
A and B are benzene; naphthalene; or benzene or naphthalene substituted by chloro, bromo, nitro methyl, trifluoromethyl, acetylamino, hydroxy, methoxy or diethylamino;
R is acetyl, propionyl, butyryl, formyl or benzoyl;
the o-position relative to Hal is free of activating substituents selected from the group consisting of nitro, nitrile and carbonyl Hal is chloro or bromo.

2. Process of claim 1 in which the reaction is conducted in the presence of a halogen catalyst.

3. Process of claim 1 in which the reaction is conducted in the presence of iodine as a catalyst.

4. Process of claim 1 in which the reaction is carried out at a temperature of 50° C to 150° C.

5. The process of claim 1 in which said inert solvent is a polar organic solvent or a mixture of polar organic solvent and water.

6. The process of claim 1 in which said inert solvent is dimethylformamide, dimethylacetamide, N-methyl-pyrrolidone, dimethylsulphoxide, sulpholane, phosphoric acid tris-dimethylamide or nitrobenzene.

7. The process of claim 1 in which an excess of copper is employed relative to the amount equivalent to the halogen to be split off.

8. Process according to claim 1 for preparing 2,2'-bis-(acetylamino)-5,5'-dichlorobiphenyl in which said acyamino-aryl and said aryl compounds are 2-bromo-4-chloroacetanilide.